(12) United States Patent
Utz

(10) Patent No.: US 10,639,416 B2
(45) Date of Patent: *May 5, 2020

(54) SYSTEM FOR ILLUMINATING MEDICAL INFUSION LINES

(71) Applicant: Hans Utz, Decatur, GA (US)

(72) Inventor: Hans Utz, Decatur, GA (US)

(*) Notice: Subject to any disclaimer, the term of this patent is extended or adjusted under 35 U.S.C. 154(b) by 22 days.

This patent is subject to a terminal disclaimer.

(21) Appl. No.: 16/203,581

(22) Filed: Nov. 28, 2018

(65) Prior Publication Data

US 2019/0091398 A1 Mar. 28, 2019

Related U.S. Application Data

(63) Continuation of application No. 15/067,512, filed on Mar. 11, 2016, now Pat. No. 10,232,107.

(51) Int. Cl.
*A61M 5/14* (2006.01)
*F21V 33/00* (2006.01)
*F21Y 115/20* (2016.01)
*F21W 131/208* (2006.01)
*F21S 4/20* (2016.01)
*F21S 4/22* (2016.01)
*F21V 8/00* (2006.01)
*F21K 2/06* (2006.01)
*A61M 5/162* (2006.01)

(52) U.S. Cl.
CPC ........ *A61M 5/1415* (2013.01); *F21V 33/0068* (2013.01); *A61M 5/14* (2013.01); *A61M 5/162* (2013.01); *A61M 2205/587* (2013.01); *A61M 2205/6009* (2013.01); *A61M 2205/6063* (2013.01); *F21K 2/06* (2013.01); *F21S 4/20* (2016.01); *F21S 4/22* (2016.01); *F21V 33/0064* (2013.01); *F21W 2131/208* (2013.01); *F21Y 2115/20* (2016.08); *G02B 6/001* (2013.01)

(58) Field of Classification Search
CPC ........ F21S 4/20; F21S 4/22; F21S 4/24; F21S 4/26; F21S 4/28; F21V 33/0068; F21V 33/0072; F21V 33/0064; F21W 2131/208; G02B 6/001; G02B 6/0005; A61M 2205/587; A61M 2205/6063; A61M 5/14; A61M 5/1415; A61B 1/07
See application file for complete search history.

(56) References Cited

U.S. PATENT DOCUMENTS

| 5,423,750 | A | 6/1995 | Spiller |
| 5,718,562 | A | 2/1998 | Lawless et al. |
| 7,783,346 | B2 | 8/2010 | Smith et al. |
| 7,833,196 | B2 | 11/2010 | Estes et al. |
| 10,232,107 | B2 * | 3/2019 | Utz ..................... A61M 5/1415 |

(Continued)

OTHER PUBLICATIONS

Office Action dated Mar. 30, 2018 for U.S. Appl. No. 15/067,612.
(Continued)

*Primary Examiner* — Jong-Suk (James) Lee
*Assistant Examiner* — James M Endo
(74) *Attorney, Agent, or Firm* — Bryan L. Baysinger

(57) ABSTRACT

Disclosed are various embodiments for illuminated medical infusion including, for example, a medical infusion system which includes a source of illumination and an illuminating infusion line and wherein the illuminating infusion line includes an integrated fluid transmission channel and light transmission channel.

14 Claims, 13 Drawing Sheets

(56) References Cited

U.S. PATENT DOCUMENTS

| | | |
|---|---|---|
| 2003/0183294 A1 | 10/2003 | Carlson |
| 2007/0088286 A1 | 4/2007 | Brier |
| 2007/0103926 A1 | 5/2007 | Brooks et al. |
| 2007/0106263 A1 | 5/2007 | Ward |
| 2007/0107517 A1 | 5/2007 | Arnold et al. |
| 2008/0123323 A1* | 5/2008 | Brunet .................. G01V 15/00 362/84 |
| 2009/0312630 A1* | 12/2009 | Hidem .................. A61M 5/007 600/431 |
| 2010/0006171 A1 | 1/2010 | Tomlin et al. |
| 2011/0196306 A1 | 8/2011 | De La Huerga |
| 2012/0065482 A1* | 3/2012 | Robinson ........... A61B 5/14532 600/309 |
| 2012/0211422 A1 | 8/2012 | Thys |
| 2013/0123743 A1* | 5/2013 | Adams .............. A61M 5/16831 604/500 |
| 2013/0208497 A1* | 8/2013 | Provost .................. A61M 5/14 362/555 |
| 2013/0209045 A1 | 8/2013 | Dean, Jr. et al. |
| 2013/0225937 A1 | 8/2013 | Schaeffer et al. |
| 2013/0331790 A1* | 12/2013 | Brown .................. A61M 5/142 604/151 |
| 2015/0083265 A1 | 3/2015 | Waldrip |
| 2015/0119795 A1 | 4/2015 | Germain et al. |
| 2017/0021095 A1 | 1/2017 | Utz |
| 2017/0023216 A1 | 1/2017 | Utz |
| 2017/0340815 A1 | 11/2017 | Utz |
| 2017/0281855 A1 | 12/2017 | Utz |

OTHER PUBLICATIONS

Office Action dated Aug. 4, 2017 for U.S. Appl. No. 15/067,589.
Office Action dated Dec. 27, 2017 for U.S. Appl. No. 15/067,573.
Office Action dated Apr. 2, 2018 for U.S. Appl. No. 15/067,533.

\* cited by examiner

SYSTEM FOR ILLUMINATING MEDICAL INFUSION LINES

CROSS-REFERENCE TO RELATED APPLICATION

This application is a continuation of and claims the benefit and priority of U.S. patent application Ser. No. 15/067,512 filed on Mar. 11, 2016, now U.S. Pat. No. 10,232,107 issued on Mar. 19, 2019, entitled "ILLUMINATED MEDICAL INFUSION," which claims the benefit of Provisional Application 62/231,338 filed on Jul. 2, 2015, entitled "METHOD FOR IDENTIFYING CHANNELS AND/OR LINES USING ILLUMINATION," the contents of which is herein incorporated by reference in its entirety.

BACKGROUND

The present invention generally relates to the administration of medical infusion. Medical infusion typically serves to administer medications, fluids, nutrients, solutions, and other materials intravenously to a patient. Patients are often administered medical infusion using intravenous infusion lines. Such intravenous infusion lines generally consist of flexible, plastic tubing connected at one end to a fluid source and at another end to a needle or port that provides access to a blood vessel of a patient. It is not uncommon for many infusion lines, each connected to a different source of fluid, to be used simultaneously to deliver several medications at once to a single patient. It is also not uncommon for the needles or ports to be located adjacent one another, such as multiple adjacent needles providing access into the brachial vein running through the arm of the patient.

Distinguishing between multiple infusion lines is a difficult task, and medication delivery error as a result of improperly distinguishing one infusion line from another is a serious problem in current infusion systems. The confusion of one infusion line from another is one of the leading causes of preventable medication error. It is potentially life-threatening and is a serious and ongoing concern and cost to medical facilities. As a result of the difficulties in distinguishing between multiple infusion lines, their associated fluid sources and outputs, and the potentially life-threatening possibilities that can occur if incompatible medications are injected through the same infusion line, there is a need for accurate identification of infusion lines.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure.

DETAILED DESCRIPTION

Figure 1:
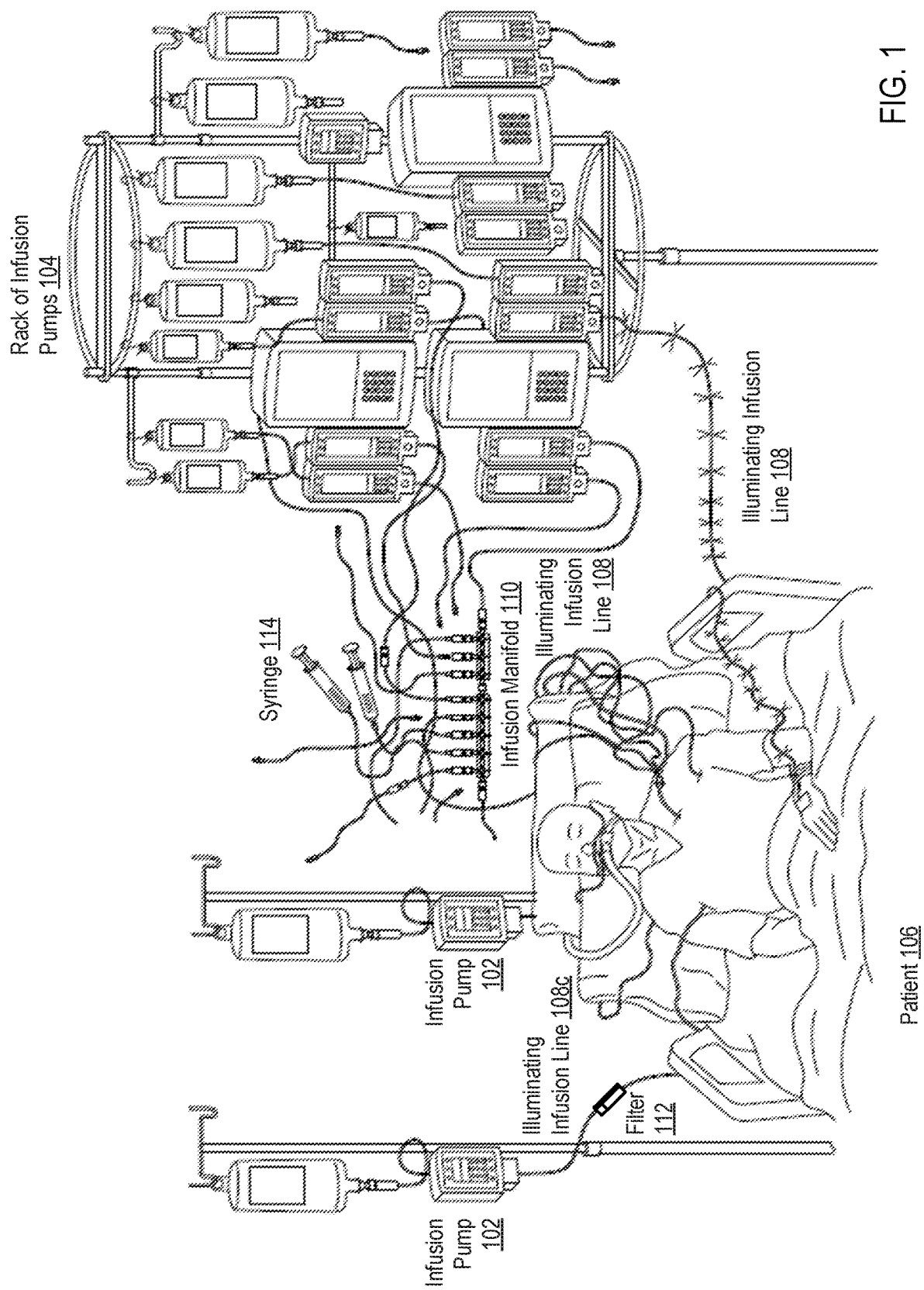
FIG. 1 sets forth a line drawing illustrating an example system for illuminated medical infusion according to embodiments of the present invention.

Illuminated medical infusion, according to example embodiments of the present invention, is described with reference to the attached drawings, beginning with FIG. 1. FIG. 1 sets forth a line drawing illustrating an example system for illuminated medical infusion according to embodiments of the present invention. The example of FIG. 1 depicts an extremely complex situation for medical infusion that is very commonplace in modern medicine. Often in hospital emergency rooms and intensive care units the sheer number of infusion lines, infusion pumps, and other infusion components providing medication and other infusion materials to a single patient is becoming a complex administrative challenge to the medical practitioner. Typical protocols for administering the infusion lines in situations such as the one depicted in FIG. 1 instruct the medical practitioner to physically handle or trace the line from its source all the way to the patient and then back to the source to ensure that the infusion and its delivery are proper. As will occur to readers of skill in the art, when the medical infusion becomes as complex as it is in FIG. 1, an illuminated medical infusion system provides an additional aid to a medical practitioner to ensure that the proper infusion is taking place line-by-line.

The illuminated medical infusion system of FIG. 1 includes two stand-alone medical infusion pumps (102) and a rack of medical infusion pumps (104). A medical infusion pump is a medical device used to deliver fluids into a patient's body in a controlled manner. There are many different types of infusion pumps which are used for a variety of purposes and in a variety of environments. Infusion pumps may be capable of delivering fluids in large or small amounts, and may be used to deliver nutrients or medications such as insulin or other hormones, antibiotics, chemotherapy drugs, and pain relievers. Examples of medical infusion pumps include syringe pumps, elastomeric pumps, a peristaltic pumps, multi-channel pumps, smart pumps, enteral pumps, patient-controlled analgesia (PCA) pumps, insulin pumps and others as will occur to those of skill in the art.

A syringe infusion pump is typically implemented as an external infusion pump which utilizes a piston syringe as the fluid reservoir and to control fluid delivery. An elastomeric infusion pump utilizes the energy in an elastic membrane to provide the force for fluid delivery. A smart pump is typically implemented as an infusion pump equipped with IV medication error-prevention software that alerts operators when a pump setting is programmed outside of pre-configured limits. In a peristaltic pump, a set of rollers pinch down on a length of flexible tubing, pushing fluid forward.

Multi-channel pumps allow fluids to be delivered from multiple reservoirs at multiple rates. An enteral infusion pump is an infusion pump that delivers liquid nutrients and medicines into the patient's digestive tract. Patient-controlled analgesia (PCA) infusion pumps are intended for the delivery of analgesics (pain relievers) and are often equipped with a feature that allows for additional limited delivery of medication upon patient demand. Insulin infusion pumps are typically implemented as ambulatory electromechanical pumps typically used to deliver insulin to patients with diabetes. Such insulin infusion pumps are used mainly by home care patients but may also be used in a healthcare facility.

The infusion pumps (102) and the rack of infusion pumps (104) may be implemented as any of the pumps described above or other type of infusion pump as will occur to those of skill in the art. In the example of FIG. 1, the infusion pumps (102) and the rack of infusion pumps (104) deliver medication or other infusion materials to a patient (106) through a number of illuminating infusion lines (108). An illuminating infusion line is an infusion line that can be illuminated upon being exposed to a source of illumination. By illuminating an infusion line, a medical practitioner can more accurately and safely administer the infusion lines and trace those infusion lines end-to-end thereby reducing infusion line mix-ups and reducing medication delivery errors.

The illuminating infusion lines (108 and 108*c*) of FIG. 1 are implemented as infusion lines each with an integrated fluid transmission channel and a light transmission channel. The fluid transmission channel provides a channel for the delivery of medications or other fluids to the patient (106). The light transmission channel is illuminated when the light transmission channel is exposed to a source of illumination. In this manner, when a source of illumination is applied to the illuminating infusion line the infusion line illuminates allowing a medical practitioner to more readily identify the infusion line for medical services to the patient. Medical services performed by the medical practitioner can include adjusting the delivery of fluids to the patient, changing the infusion line, and any other operations as will occur to those of skill in the art.

A channel as that term is used in this specification means a pathway, passage, medium or other form of transmission of fluid, light, information, or any other transmittable as will occur to those of skill in the art. In some embodiments, a channel may be implemented as a conduit allowing the transmission of light, such as, for example, an optical fiber for fiber optic light transmission. Another example of a channel according to embodiments of the present invention is implemented as a conduit that includes a hollow fluid transmission line allowing for the flow or transmission of fluids through the conduit. Alternatively, a channel may be implemented simply as a medium for transmission. For example, the structure that forms a conduit around a fluid transmission line, as discussed in more detail below, may itself be a channel for transmission of light for illuminating the conduit itself.

In the example of FIG. 1, the fluid transmission channel and the light transmission channel of the illuminating infusion line (106) are integrated. That is, the fluid transmission channel and the light transmission channel are attached to one another such that the two channels coexist with one another for the useful life of the illuminating infusion line. Integration of the light transmission channel and the fluid transmission channel thereby reduces any need for the medical practitioner to administer any components of the line itself to make the infusion line illuminate and can concentrate only on attachment, replacement, or other administration of the illuminating infusion line in a manner similar to conventional infusion lines with the benefit of having the line illuminated when exposed to a source of illumination. Furthermore, the illuminating infusion lines of the present invention do not require a medical practitioner to do any additional set up, such as combining a light transmission channel with a fluid transmission channel because they are already integrated as will occur to those of skill in the art.

In the example of FIG. 1, an infusion manifold (110) receives a number of illuminating infusion lines from the rack of infusion pumps (104). An infusion manifold is a medical infusion apparatus in which a plurality of valves or other infusion components are integrated. Such manifolds often provide one or more attachments for infusion lines each connected with one or more infusion pumps. Such manifolds also often provide attachments for other infusion lines connected from the manifold to the patient. The inclusion of a manifold is for explanation and not for limitation. Illuminated medical infusion according to embodiments of the present invention may be implemented without manifolds as will occur to those of skill in the art.

In the example of FIG. 1, the infusion manifold (110) provides an access point for infusion from a syringe (114), such as, for example, an intravenous bolus, which is sometimes called an intravenous push. An intravenous bolus is typically considered a relatively large dose of medication administered into a vein for a short period, usually within 1 to 30 minutes. The IV bolus is commonly used when rapid administration of a medication is needed, such as in an emergency, when drugs that cannot be diluted, such as many cancer chemotherapeutic drugs, are administered, and when the therapeutic purpose is to achieve a peak drug level in the bloodstream of the patient. In administering such an intravenous bolus, illuminated medical infusion provides a visual aid to a medical practitioner careful to administer the bolus on the correct infusion line. Illuminated medical infusion according to embodiments of the present invention also aids a medical practitioner in identifying the correct infusion point along a complex medical infusion line.

As mentioned above, the illuminating infusion lines of FIG. 1 may be illuminated with a source of illumination. A source of illumination is a device that provides the impetus to illuminating an infusion line according to embodiments of the present invention. As discussed in more detail below, such sources of illumination may be handheld sources of illumination administered by a medical practitioner, attachable sources of illumination for attachment onto the illuminating infusion line, sources of illumination integrated into the illuminating infusion line, sources of illumination integrated into an infusion pump, sources of illumination integrated into an infusion manifold, or any other source of illumination that will occur to those of skill in the art. A source of illumination may be implemented as a source of light, such as, for example, a laser, a light emitting diode ('LED'), an organic light emitting diode ('OLED'), or other source of light that will occur to those of skill in the art. Such sources of light are especially useful in illuminating light transmission channels of illuminating infusion lines according the embodiments of the present invention implemented with, for example, optical fibers. Sources of illumination, however, are not limited only to sources of light. Sources of illumination may also include sources of electrical potential inducing an electrical current for illumination of the infusion line through electroluminescence. Sources of illumination may include sources of stimulating fluorescence as will occur to those of skill in the art. Even further, sources of illumination may include chemical reactions for illuminating the infusion line through chemiluminescence or other forms of chemical luminescence. The above are just a few references for sources of illumination; other sources of illumination will occur to those of skill in the art.

In the example of FIG. 1, one of the illuminating infusion lines (108*c*) is attached to an infusion filter (112). An infusion filter is one of many in-line components that often reside between or within illuminating infusion lines for illuminated medical infusion according to embodiments of the present invention. An infusion filter is one of a number of devices used to help ensure the purity of intravenous solutions. Such filters are often used to strain the solution to remove contaminants, such as dissolved impurities, extraneous salts, microorganisms, particles, precipitates, undissolved drug powders and other contaminants that will occur to those of skill in the art. Such filters are also often used to eliminate or reduce air bubbles in the infusion line as will occur to those of skill in the art.

In some embodiments of the present invention, a single illuminating infusion line may be manufactured with a filter in-line within it such that the light transmission channel is not interrupted by the filter, thereby allowing the entire length of the illuminating infusion line to illuminate. In other embodiments, the light transmission channel is interrupted by the filter or other in-line component or impediment installed in the line. In still other embodiments, the filter resides between two illuminating infusion lines. In some embodiments where the light transmission channel of one or more illuminating infusion lines is interrupted by a filter or other in-line component or impediment, a source of illumination may be used to illuminate the infusion lines on either side of the impediment, as is discussed in more detail below. In some embodiments, two sources of illumination may reside on either end of the in-line component, and each may asynchronously illuminate their respective infusion lines. In other embodiments, the two sources of illumination may operate synchronously such that both sources of illumination illuminate their respective infusion lines together. Such synchronous sources of illumination may operate by being coupled for data communications through wired or wired connection as will occur to those of skill in the art. Other sources may bypass the in-line filter, in-line component, or line impediment by the practitioner directing the source of illumination to a location on the line, and correspondingly repeating the process on the other side of the in-line filter or impediment. Other sources of illumination may originate within or on the manifold, infusion pump, or any other infusion component and work synchronously with other sources of illumination in order to illuminate the entirety of the line. The example filter of FIG. 1 is for explanation and not for limitation. Many in-line components may themselves be illuminated for illuminated medical infusion according to embodiments of the present invention including valves, access points, manifolds and other components for medical infusion that will occur to those of skill in the art.

Figure 2:
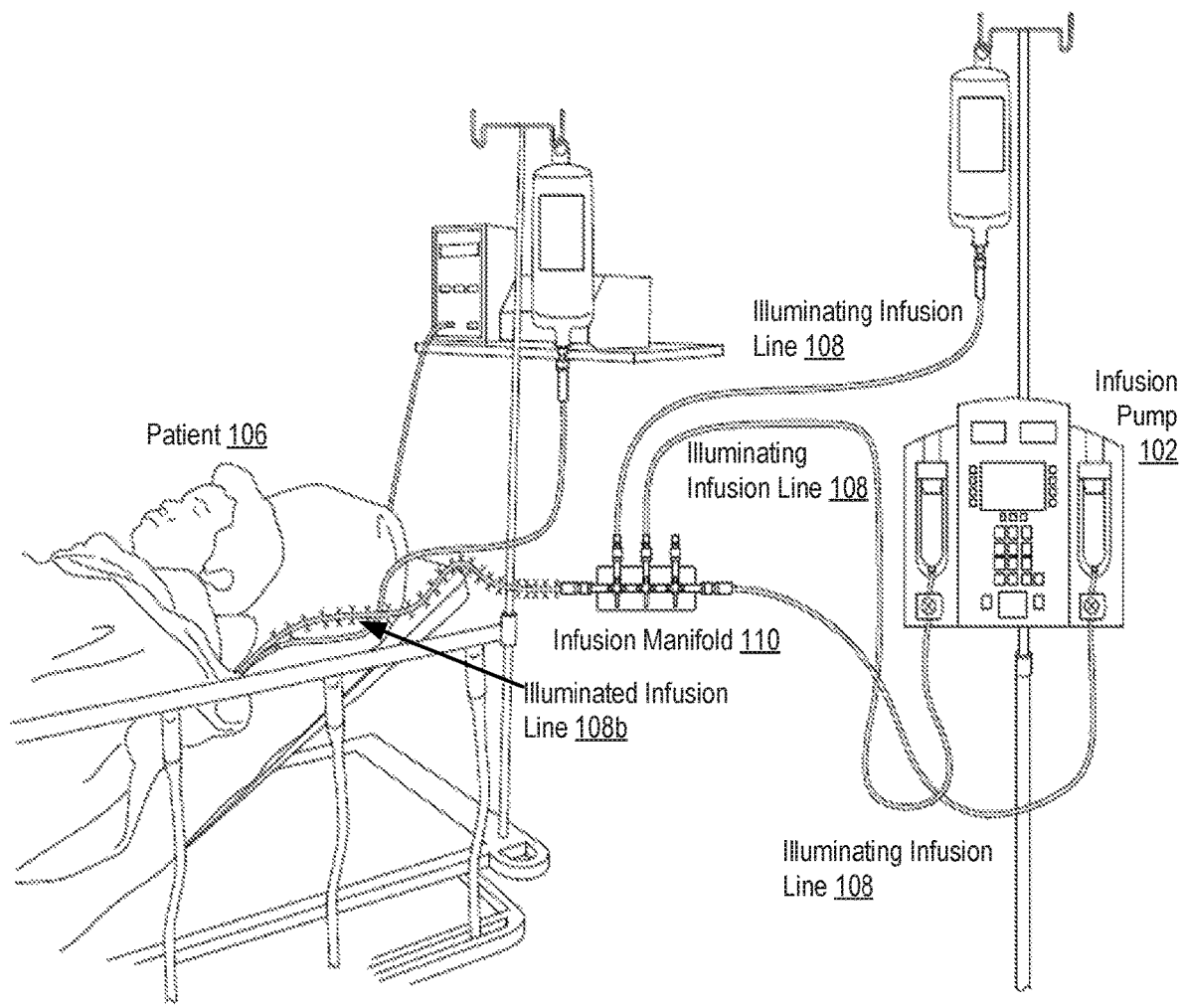
FIG. 2 sets forth a line drawing illustrating another example of illuminated medical infusion according to embodiments of the present invention.

FIG. 1 illustrates illuminated medical infusion in the context in which it may be most useful and best understood—very complicated infusion situations such as those that are common in hospital emergency rooms or intensive care units. That is, the example of FIG. 1 illustrates illuminated medical infusion with many infusion lines, infusion pumps, an infusion manifold, a filter and so on. In such situations, the ability to have an illuminating infusion line which has a static and integrated light transmission channel is extremely useful to the medical practitioner and provides increased safety to the patient. For further explanation, however, FIG. 2 sets forth a line drawing illustrating another depiction of illuminated medical infusion according to embodiments of the present invention. For purposes of explanation, the example of FIG. 2 is a simpler depiction of illuminated medical infusion than is depicted in the example of FIG. 1. In the example of FIG. 2, fewer components for illuminated medical infusion are included for the sake of clarity. In the example of FIG. 2 four illuminating infusion lines according to embodiments of the present invention are attached to an infusion manifold (110). Two of the illuminating infusion lines are also attached to an infusion pump (102). In the example of FIG. 2, each of the illuminating infusion lines are capable of illumination with a source of illumination which may be either handheld, attached to the line, integrated into the line itself, integrated into an infusion manifold or other infusion component, integrated into an infusion pump or other source of illumination as will occur to those of skill in the art. By illuminating each infusion line between a medication or other solution being administered and the patient, a medical practitioner can trace the line from the medication to the patient, and such tracing is aided with visual aid of the illumination of the line. Readers of skill in the art will recognize that the medical illumination illustrated in FIG. 2 becomes increasingly useful and valuable as the complexity of the infusion situation increases such as that in the example of FIG. 1.

In the example of FIG. 2, the infusion line (108*b*) is depicted as being currently illuminated. Such illumination occurs by exposing a source of illumination to an illuminating infusion line according to embodiments of the present invention. As discussed in more detail below, such sources of illumination may be handheld sources of illumination administered by a medical practitioner, attachable sources of illumination for attachment onto the illuminating infusion line, sources of illumination integrated into the illuminating infusion line, sources of illumination integrated into an infusion pump, sources of illumination integrated into an infusion manifold, or any other source of illumination that will occur to those of skill in the art.

Those of skill in the art will recognize that illuminating an infusion line provides increased aid to a medical practitioner tracing the line from the origin of the solution being administered through the infusion line to the patient. Those of skill in the art will also recognize that having the light transmission channel that illuminates the infusion line integrated with the fluid transmission line minimizes the risk of having a line identification system not attached to the infusion line itself which also provides increased aid to the medical practitioner in tracing the line and thereby provides increased safety to the patient. Those of skill in the art will even further recognize that having the light transmission channel that illuminates the infusion line integrated with the fluid transmission line reduces the need or risk of a medical practitioner improperly attaching auxiliary light transmission channel to an infusion line as the light transmission channel is already integrated into the infusion line.

Figure 3:
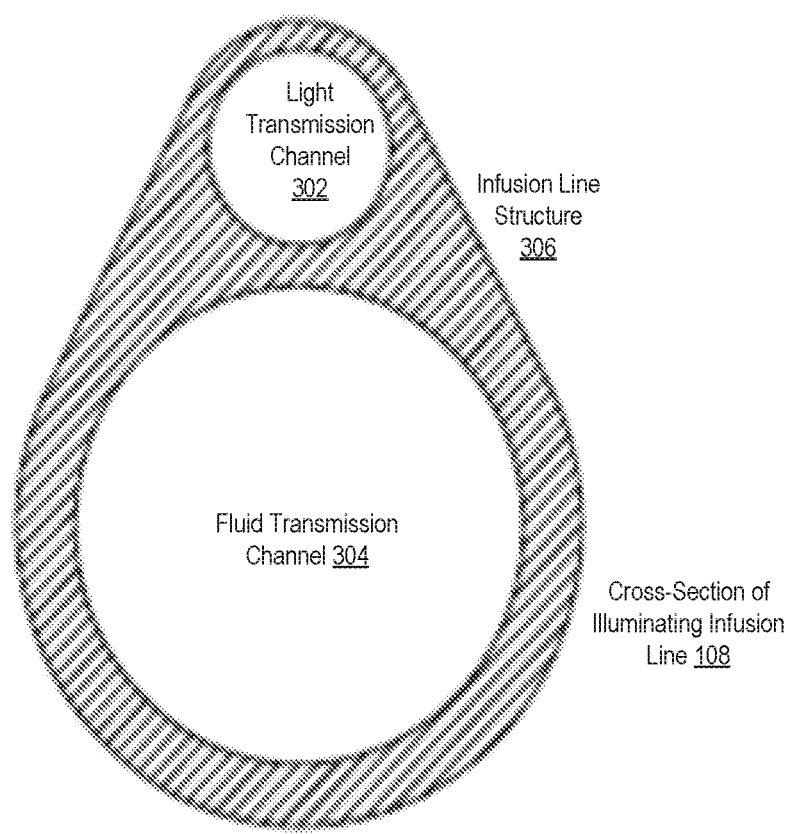
FIG. 3 sets forth a line drawing of a cross section of an illuminating infusion line according to embodiments of the present invention.

The integration of light transmission channels and fluid transmission channels in illuminating infusion lines according to embodiments of the present invention may be implemented in a number of forms. For further explanation, FIG. 3 sets forth a line drawing of a cross section of an illuminating infusion line according to embodiments of the present invention. In the example of FIG. 3, the illuminating infusion line (108) has a fluid transmission channel (304) and a light transmission channel (302) that are integrated by the infusion line structure (306). In some embodiments of the present invention, an illuminating infusion line such as the one depicted in FIG. 3 may be created through an extrusion process. An extrusion process is typically used to create objects of a fixed or semi-fixed cross sectional profile. A material is typically pushed through a die of the desired cross section. Extrusion provides the ability to create very complex cross sections. Extrusion often also forms parts with good surface finish. The infusion line structure (306) of the example of FIG. 3 may be made through extrusion from a number of materials as will occur to those of skill in the art. Examples of suitable materials include plastic compositions such as linear, branched, and cross-linked polymers, isomers, polymer blends, and others that will occur to those of skill in the art.

The light transmission channel of the example of FIG. 3 may be implemented as an optical fiber residing or extruded within the infusion line structure (306). In such embodiments, the infusion line structure (306) is made of a material which is to some degree transparent for visual aid to the medical practitioner. That is, in such embodiments, when the optical fiber or other material residing in the light transmission channel is illuminated, the illumination is visible through the infusion line structure such that the illuminating infusion line may be traced by the medical practitioner. Any variable degree of opacity is applicable and would be understood to those of skill in the art.

The description of the use of an optical fiber residing in the light transmission channel is for explanation and not for limitation. The light transmission channel may also be implemented with a number of materials including photoluminescent materials, chemiluminescent materials, electroluminescent materials and other luminescent materials as will occur to those of skill in the art. Photoluminescence is light emission from any form of matter after the absorption of photons (electromagnetic radiation). Photoluminescence is one of many forms of luminescence (light emission) and is initiated by photoexcitation (excitation by photons). Following excitation, various relaxation processes typically occur in which other photons are re-radiated. Time periods between absorption and emission may vary: ranging from short femtosecond-regime for emission involving free-carrier plasma in inorganic semiconductors up to milliseconds for phosphorescent processes in molecular systems, and under special circumstances delay of emission may even span to minutes or hours.

The light transmission channel may also be implemented with a chemiluminescent material. Chemiluminescence (sometimes "chemoluminescence") is the emission of light (luminescence), as the result of a chemical reaction. Chemiluminescence differs from photoluminescence and electroluminescence in that the excited state is a product of a chemical reaction. Various types of chemical reactions can occur, such reactions can occur under liquid phase reactions and gas phase reactions.

The light transmission channel may also be implemented with an electroluminescent material. Electroluminescence is an optical phenomenon and electrical phenomenon in which a material emits light in response to the passage of an electric current or to the presence of an electric field. Electroluminescent material may be implemented as one or more electroluminescent wires embedded within the structure of the illuminating infusion line. Such electroluminescent wire may be implemented, for example, as a thin copper wire coated in a phosphor which glows when an alternating current is applied to it.

The light transmission channel may also be implemented through electromagnetic illumination, chemical illumination, fluorescence, or any other form of illumination that will occur to those of skill in the art.

The example illuminating infusion line of FIG. 3 also includes a fluid transmission channel (304). The fluid transmission channel of FIG. 3 is implemented as a conduit or hollow passage through the infusion line structure that allows the transmission of fluids through the line. Such a fluid transmission channel may be manufactured for direct attachment to current medical infusion platforms and components including filters, infusion pumps, manifolds, and other infusion components that will occur to those of skill in the art.

Figure 4:
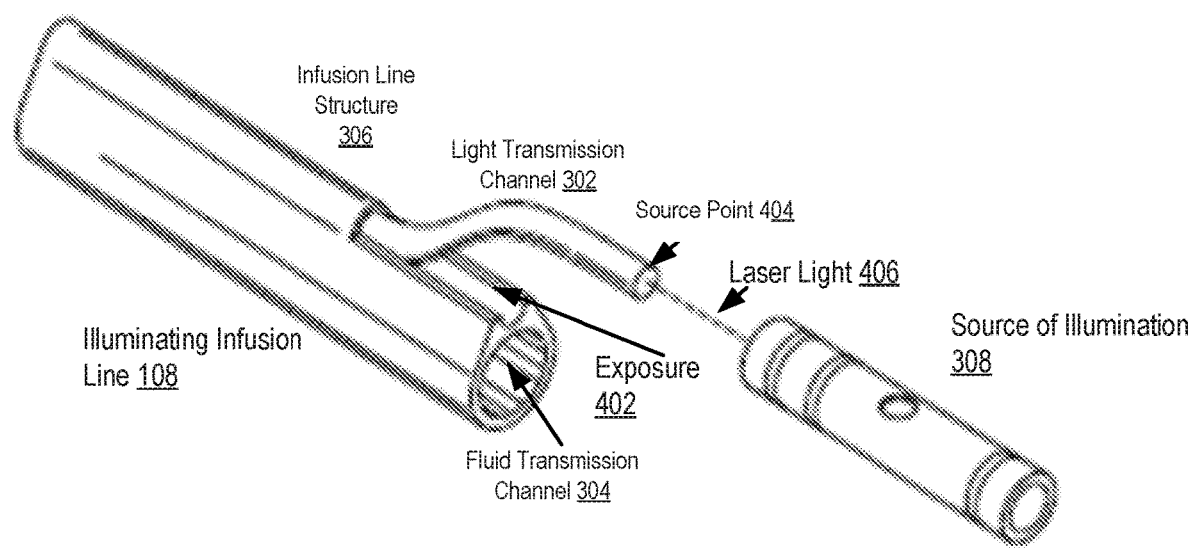
FIG. 4 sets forth a line drawing of an illuminating infusion line having a cross section similar to the illuminating infusion line of the example of FIG. 3.

For further explanation, FIG. 4 sets forth a line drawing of an illuminating infusion line having a cross section similar to the illuminating infusion line of the example of FIG. 3. The illuminating infusion line (108) of FIG. 4 is similar to the infusion line of FIG. 3 in that the infusion line of FIG. 4 has a light transmission channel (302) and a fluid transmission channel (304) which are integrated through the infusion line structure (306). The illuminating infusion line of FIG. 4 however also has an exposure (402) allowing the light transmission channel (302) to be separated from the fluid transmission channel (304) such that a source of illumination (308) may be used to directly illuminate the light transmission channel and therefore illuminating the infusion line.

In the example of FIG. 4, the source of illumination (308) is implemented as a source of laser light (406) and the light transmission channel (302) is implemented as an optical fiber. The light transmission channel of FIG. 4 has a source point (404) at the end of the light transmission channel (302) which is allowed separation from the fluid transmission channel through the exposure (402). The separation of the light transmission channel (302) from the fluid transmission channel (304) in the example of FIG. 4 allows a hand-held source of illumination (308) such as that depicted to be exposed upon the light transmission channel (302).

The laser light (406) from the source of illumination (308) in the example of FIG. 4 is directed upon the source point (404). Directing the laser light (406) on the source point (404) illuminates the fiber optic light transmission channel (302) and in turn illuminates the illuminating infusion line.

The use of fiber optics and laser light in the example of FIG. 4 is for explanation and not for limitation. As mentioned above, the light transmission channel of FIG. 4 may be implemented with photoluminescent material, chemiluminescent material, electroluminescent material or any other luminescent material or light transmission or light activation material that will occur to those of skill in the art. Sources of illumination according to embodiments of the present invention may be sources of light such as sources of white light, light emitting diodes ('LEDs'), organic light emitting diodes ('OLEDs'), laser light and others as well as sources of illumination through electricity, chemistry, sound, material properties, or others as will occur to those of skill in the art.

In the example of FIG. 4, the source of illumination (308) is shown as detached from the light transmission channel. This is for ease of explanation and not for limitation. In many embodiments of medical illumination according to the present invention the source of illumination is attached to the light transmission channel or the infusion line and such attachment may come in many forms as will occur to those of skill in the art.

Figure 5:
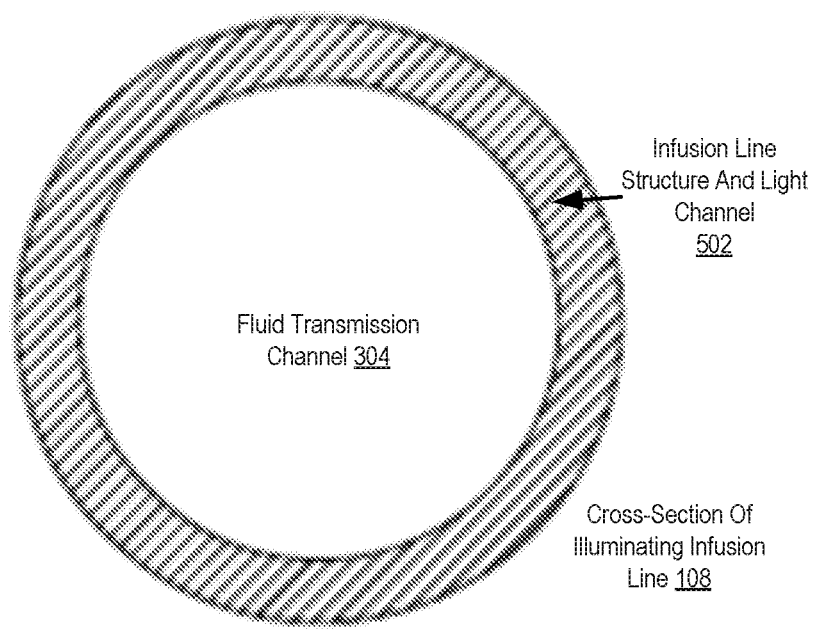
FIG. 5 sets forth a line drawing illustrating a cross section of an illuminating infusion line according to embodiments of the present invention.

The example illuminating infusion lines of FIGS. 3 and 4 have a light transmission channel (302) with a separate infusion line structure surrounding the light transmission channel and integrating that light transmission channel with a fluid transmission channel. For further explanation, FIG. 5 sets forth a line drawing illustrating a cross section of an illuminating infusion line according to embodiments of the present invention. In the example of FIG. 5, the fluid transmission channel (304) is implemented as a conduit surrounded by the infusion line structure (502). The example of FIG. 5 differs from the example of FIG. 3 in that the light transmission channel (502) is implemented as the infusion line structure itself. In the example of FIG. 5, the infusion line structure and the light transmission channel are the same structure. In this example, the material of the infusion line structure is itself a light transmission channel such that by applying a source of illumination to the infusion line structure causes the material of the infusion line structure to illuminate and in turn illuminate the infusion line itself. Such a combination infusion line structure and light transmission channel may be made of photoluminescent material as will occur to those of skill in the art. Such a material may be implemented as a fast-absorption, fast-emission material or other useful material as will occur to those of skill in the art.

Figure 6:
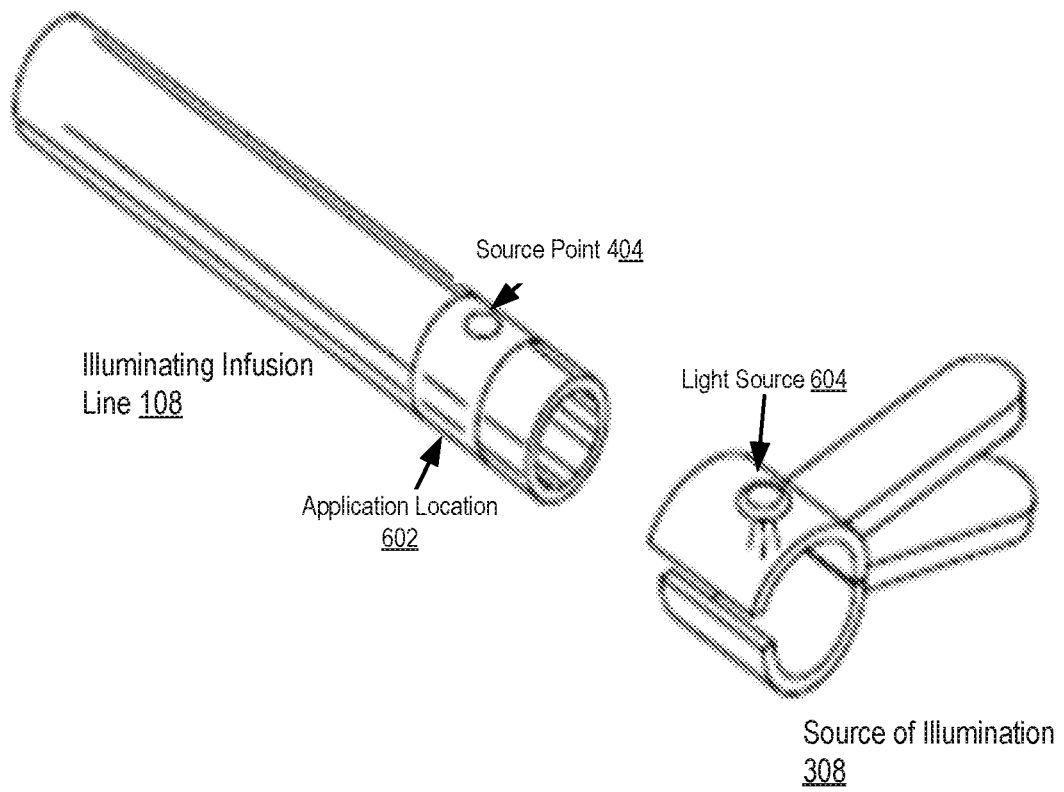
FIG. 6 sets forth a line drawing of an illuminating infusion line having a cross section similar to the infusion line of FIG. 5.

For further explanation, FIG. 6 sets forth a line drawing of an illuminating infusion line having a cross section similar to the infusion line of FIG. 5. In the example of FIG. 5, the illuminating infusion line has an application location (602) for the application of the source of illumination (308). In the example of FIG. 6, the source of illumination is implemented as a clip-type source of illumination which allows the source of illumination to be clipped onto the illuminating infusion line (108) at the application location (602). The clip-type source of illumination (308) of FIG. 6 has a light source (604) that corresponds to a source point (404) allowing light to be directed through the source point to the structure of the illuminating infusion line such that the illuminating infusion line illuminates.

The use of a light source in the example of FIG. 6 is for explanation and not for limitation. In fact, the light source (604) of FIG. 6 may be substituted for a source of current for electroluminescent illumination of the illuminating infusion line as will occur to those of skill in the art. The source of illumination of FIG. 6 may also be implemented as any source of illumination as described above for illumination of fluorescent material, chemical illumination, and others as will occur to those of skill in the art.

Figure 7:
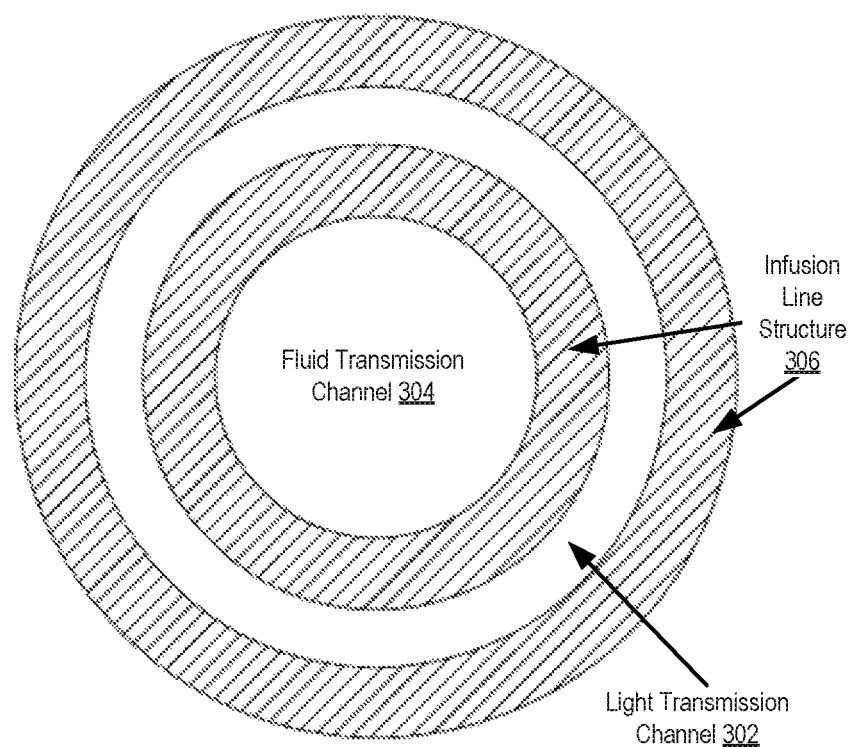
FIG. 7 sets forth a line drawing illustrating cross section of another example embodiment of an illuminating infusion line according to embodiments of the present invention.

For further explanation, FIG. 7 sets forth a line drawing illustrating the cross section of another example embodiment of an illuminating infusion line according to embodiments of the present invention. In the example of FIG. 7, the illuminating infusion line (108) has a fluid transmission channel and a light transmission channel (302) that are integrated by the infusion line structure (306). In the example of FIG. 7 the fluid transmission channel is implemented as a conduit that allows the transmission or flow of medical solution, fluid or other infusion material. In the example of FIG. 7 the light transmission channel (302) surrounds the fluid transmission channel (304). As described above, the light transmission channel (302) may be implemented with photoluminescent, chemiluminescent, electroluminescent, or any other luminescent material that will occur to those of skill in the art.

In the example of FIG. 7, the light transmission channel is shown as completely surrounding the fluid transmission channel. This is for explanation and not for limitation. In some embodiments the light transmission channel may be implemented as only partially surrounding the fluid transmission channel as will occur to those of skill in the art.

Figure 8:
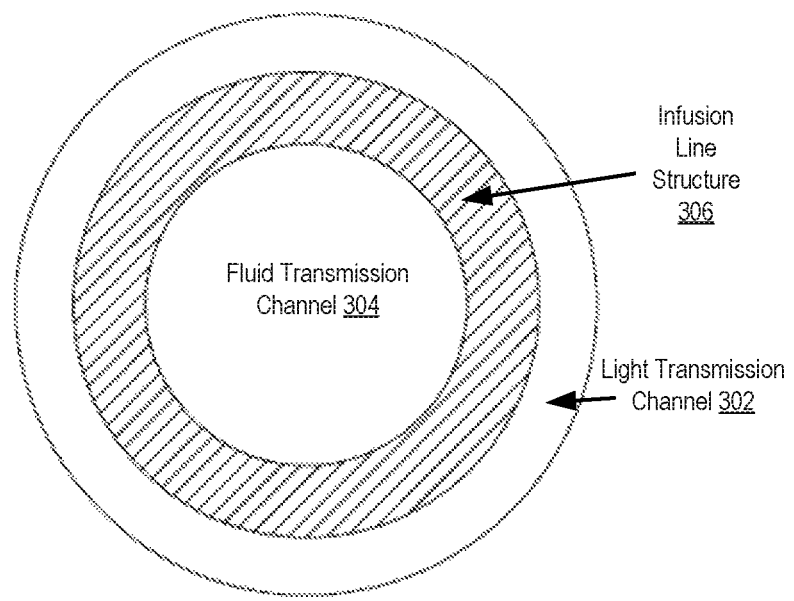
FIG. 8 sets forth a line drawing illustrating cross section of another example embodiment of an illuminating infusion line according to embodiments of the present invention.

For further explanation, FIG. 8 sets forth a line drawing illustrating a cross section of another example embodiment of an illuminating infusion line according to embodiments of the present invention. In the example of FIG. 8, the illuminating infusion line (108) has a fluid transmission channel and a light transmission channel (302) that are integrated. In the example of FIG. 7 the fluid transmission channel is implemented as a conduit surrounded by the infusion line structure (306) that allows the transmission or flow of medical fluid or other medical solution as will occur to those of skill in the art. In the example of FIG. 8, the light transmission channel (302) surrounds the fluid transmission channel. In the example of FIG. 8, the light transmission channel is implemented as a channel attached to, coated upon, extruded, deposited upon, or otherwise affixed to the exterior of the infusion line structure. Such a light transmission channel may be affixed to the exterior of the infusion line structure through vapor deposition, paint application, or in other ways as will occur to those of skill in the art. The example of FIG. 8 depicts the light transmission channel as completely surrounding the infusion line structure. This is for explanation and not for limitation. In fact, a light transmission channel may be affixed to the exterior of the infusion line structure in a number of ways. For example, the light transmission channel may be affixed to the infusion line structure by painting or otherwise coating an illuminating material down the side of the infusion lines structure and in turn the illuminating infusion line itself. As described above, the light transmission channel (302) of FIG. 8 may be implemented with photoluminescent, chemiluminescent, electroluminescent, fluorescent, chemical illuminating, or any other luminescent material that will occur to those of skill in the art.

Figure 9:
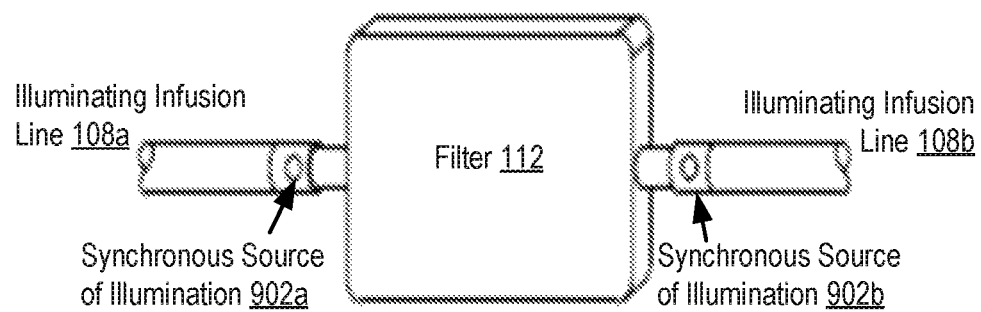
FIG. 9 sets forth a line drawing illustrating an example embodiment of a synchronous light source for illuminated medical infusion according to embodiments of the present invention.

As mentioned above with reference to FIG. 1, medical infusion often makes use of in-line components that may reside between the infusion pump, syringe or other origin of medical infusion and the patient receiving the infusion. Examples of such in-line components include filters, valves, access points, manifolds, and other in-line components as will occur to those of skill in the art. Illuminated medical infusion according to embodiments of the present invention therefore contemplates that illuminating infusion lines should be illuminated on both sides of such an in-line component such that the infusion may be traced across the in-line component. For further explanation, FIG. 9 sets forth a line drawing illustrating an example embodiment of a synchronous light source for illuminated medical infusion according to embodiments of the present invention. In the example of FIG. 9, illuminating infusion lines (108a and 108b) according to embodiments of the present invention reside on either end of a filter (112). The fluid transmission channels of each of the illuminating infusion lines (108a and 108b) are attached to the filter (112) such that medical infusion passes through the filter (112) as will occur to those of skill in the art.

Also residing on either end of the filter (112) of FIG. 9, are a pair of synchronous sources of illumination (902a and 902b). In the example of FIG. 9, the sources of illumination are synchronous in the sense that activating one of the sources of illumination (902a) activates the other source of illumination (902b) thereby illuminating both illuminating infusion lines (108a and 108b). The sources of illumination (902a and 902b) may be synchronously activated through wired or wireless communications as will occur to those of skill in the art. Examples of wired communications may be electrical, fiber optic, or others as will occur to those of skill in the art. Examples of wireless communications include Bluetooth, Wi-Fi, 3G, 4G, LTE or others as will occur to those of skill in the art.

The example of FIG. 9 depicts synchronous sources of illumination. This is for explanation and not for limitation. In other embodiments of the present invention, the sources of illumination may be independent and asynchronous as will occur to those of skill in the art.

Figure 10:
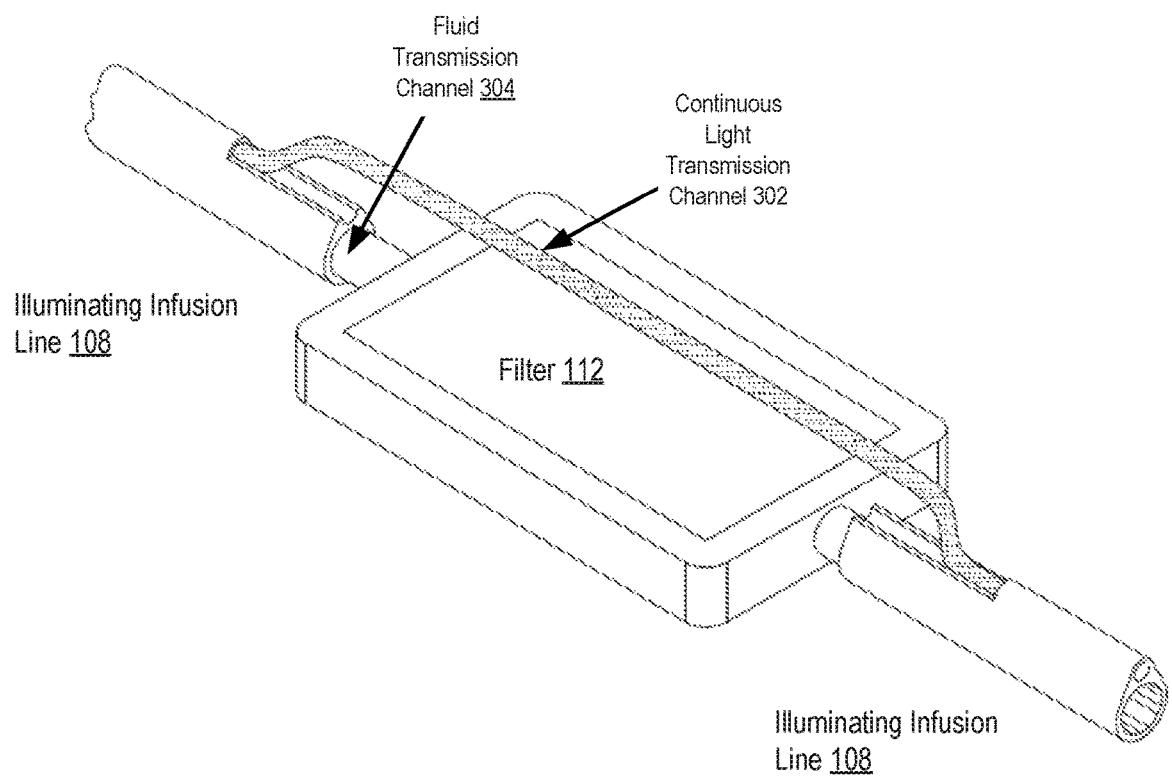
FIG. 10 sets forth a line drawing illustrating an example embodiment of an illuminating infusion line having a disconnected fluid transmission channel and a continuous light transmission channel.

In the example of FIG. 9, the light transmission channel of the illuminating infusion lines (108a and 108b) are disconnected. The description of disconnected light transmission channels is for explanation and not for limitation. For further explanation, FIG. 10 sets forth a line drawing illustrating an example embodiment of an illuminating infusion line (108) having a disconnected fluid transmission channel with a continuous light transmission channel. In the example of FIG. 10, the illuminating infusion line (108) has a disconnected fluid transmission channel (304) leaving two ends of the fluid transmission channel (304a and 304b) such that either end of the fluid (304a and 304b) may be connected to the filter (112) or other in-line infusion component. In the example of FIG. 10, the light transmission channel is continuous. That is, the light transmission channel is uninterrupted across the inline component, in this case a filter, to illuminate the line. The continuous and uninterrupted nature of the light transmission channel allows the illuminating infusion line to be illuminated across the filter using sources of illumination on any portion of the illuminating infusion line discussed above and as will occur to those of skill in the art.

Figure 11A:
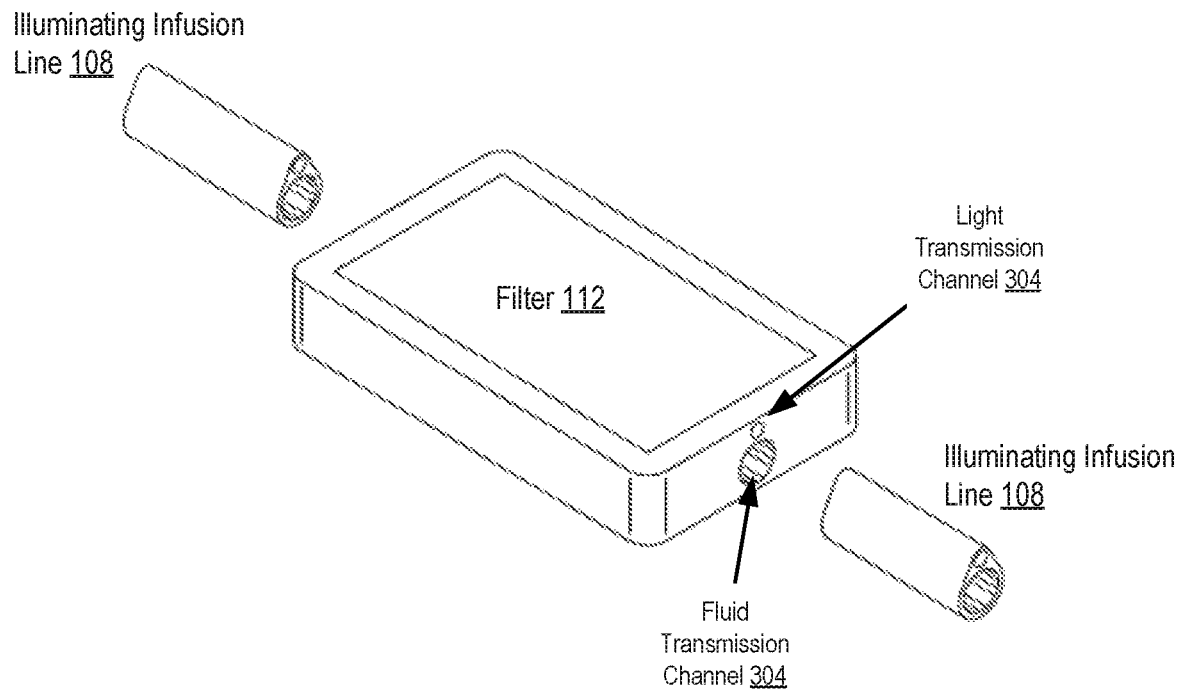
FIG. 11A sets forth a line drawing of an inline component with a light transmission channel according to embodiments of the present invention.
Figure 11B:
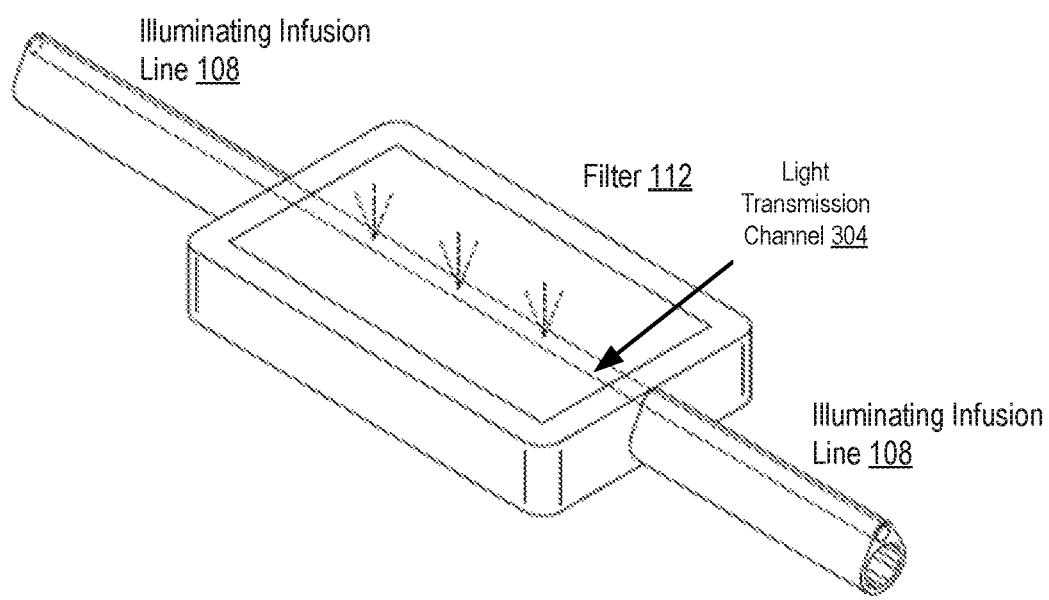
FIG. 11B sets forth a line drawing of an inline component with a light transmission channel according to embodiments of the present invention.

For further explanation, FIGS. 11A and 11B set forth line drawings of an inline component with an integrated light transmission channel. In the examples of FIGS. 11A and 11B, the inline component is illustrated as a filter. This is for explanation and not for limitation. In fact, any number of inline components may include integrated light transmission channels for illuminated medical infusion according to embodiments of the present invention. In the examples of FIGS. 11A and 11B, the illuminating infusion lines (108) may be attached to either side of the filter (112) such that the integrated light transmission channel (304) of the filter 112 is illuminated when the light transmission channel of either illuminating infusion line is illuminated to provide continuous illumination across the inline component—in this example a filter (112).

Figure 12:
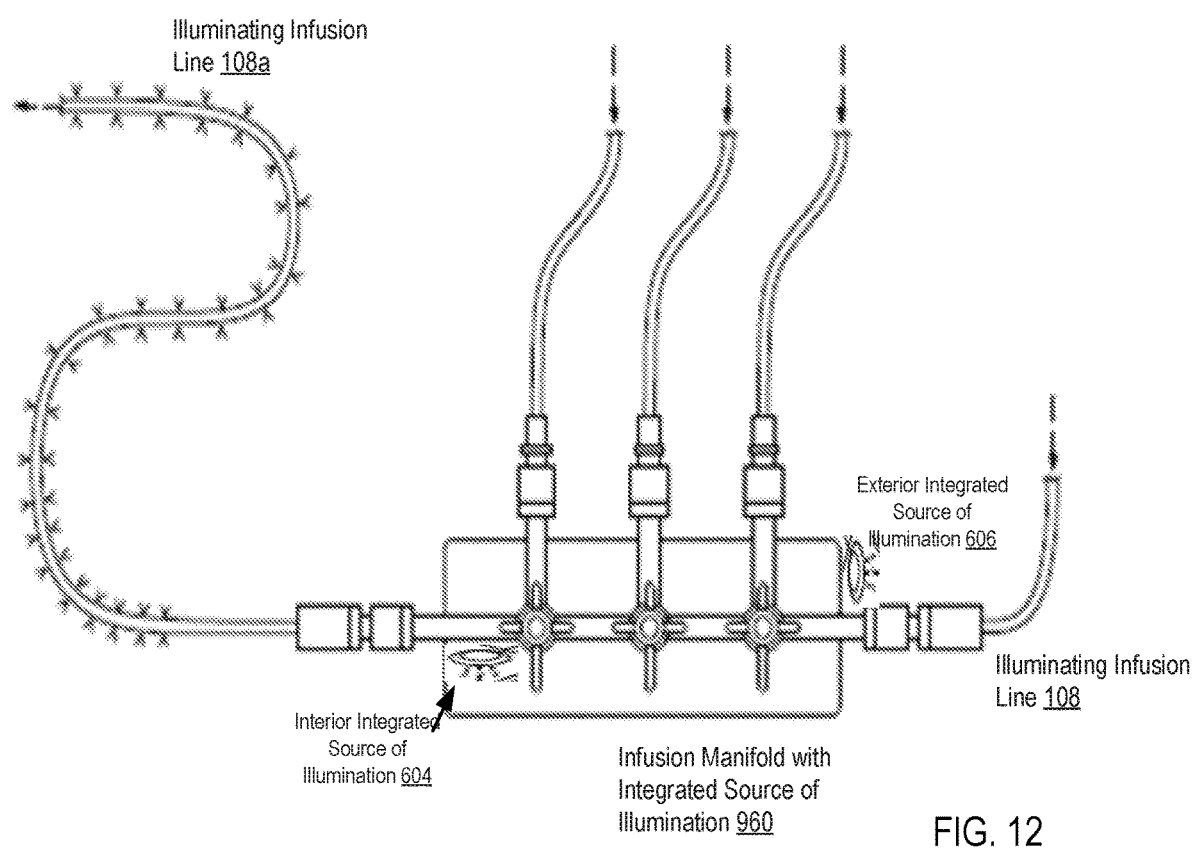
FIG. 12 sets forth a line drawing illustrating an infusion manifold with an integrated source of illumination.

As discussed above, illuminating infusion lines many be illuminated with a number of sources of illumination including handheld sources of illumination, sources of illumination attached to the illuminating infusion lines, and sources of illumination integrated into various components used in medical infusion according to embodiments of the present invention. For further explanation, FIG. 12 sets forth a line drawing illustrating an infusion manifold with an integrated source of illumination. In the example of FIG. 12, the infusion manifold has two integrated sources of illumination (604 and 606). The example infusion manifold of FIG. 12 includes an interior integrated source of illumination. That is, one example source of illumination (604) of FIG. 12 is integrated into the interior of the body of the manifold (960) and illuminates the illuminating infusion line (108a) through the interior source of illumination (604). The example of FIG. 12 also includes an exterior source of illumination (606). The example exterior integrated source of illumination (606) is a source of illumination integrated to the outside of the infusion manifold (960). As with other sources of illumination described herein, the sources of illumination in the example of FIG. 12 may be implemented as sources of light, sources of electricity, chemical, or other sources of illumination that will occur to those of skill in the art.

Figure 13:
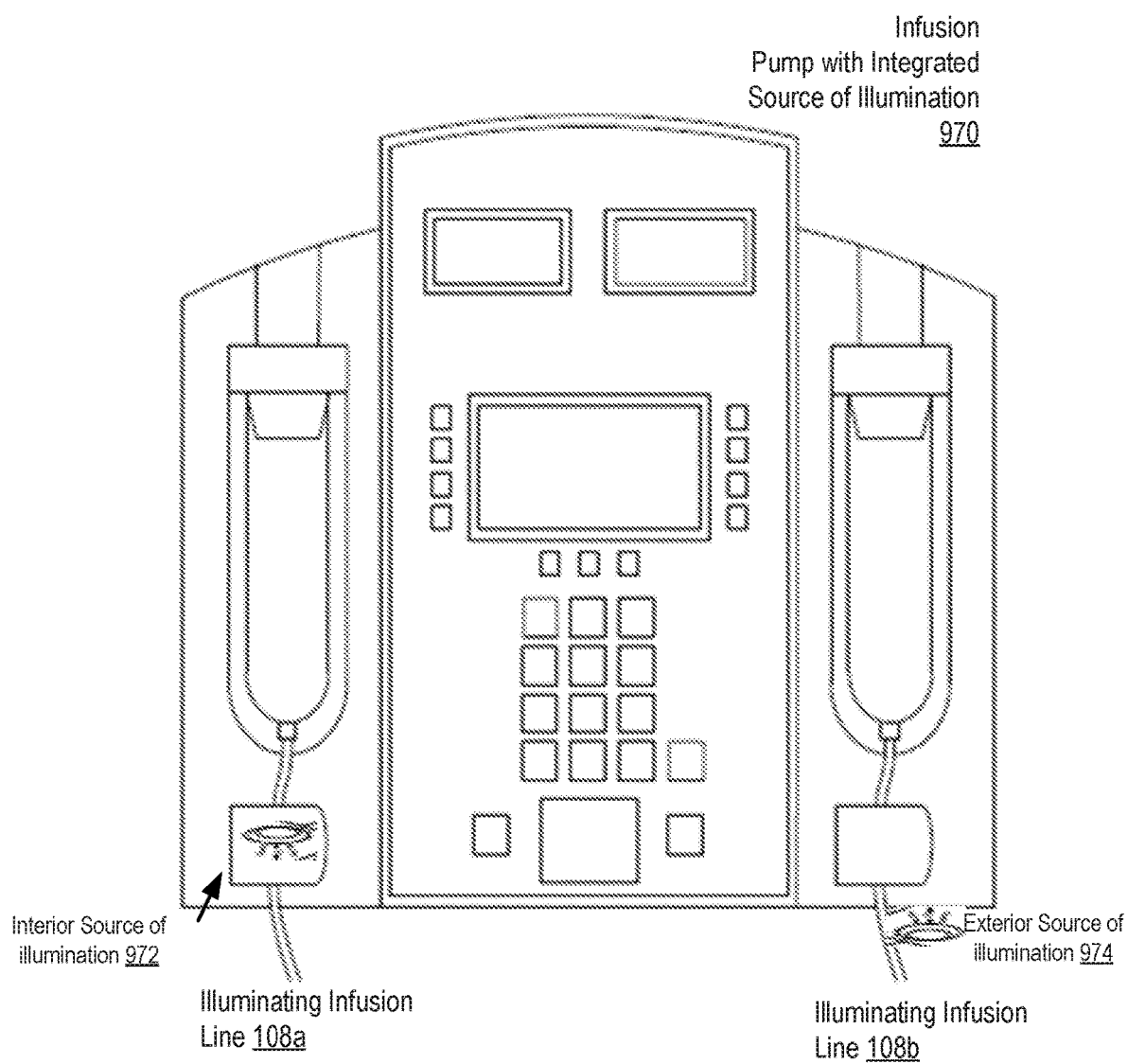
FIG. 13 sets forth a line drawing illustrating an infusion pump with an integrated source of illumination.

For further explanation, FIG. 13 sets forth a line drawing illustrating an infusion pump with an integrated source of illumination. In the example of FIG. 13, the infusion pump has two integrated sources of illumination (972 and 974). The example infusion pump of FIG. 13 includes an interior integrated source of illumination. That is, the infusion pump includes a source of illumination that is integrated into the interior of the body of the infusion pump and illuminates the illuminating infusion line (108a) through the interior source of illumination (972). In the example of FIG. 13, the infusion pump (970) also includes an exterior source of illumination (974). The exterior integrated source of illumination (974) is a source of illumination integrated to the outside of the infusion pump (970). As with other sources of illumination described herein, the sources of illumination in the example of FIG. 13 may be implemented as sources of light, sources of electricity, chemical, or other sources of illumination that will occur to those of skill in the art.

The examples of FIGS. 12 and 13 illustrate sources of illumination integrated into an infusion manifold and an infusion pump. This is for explanation and not for limitation. Sources of illumination according to embodiments of the present invention may be integrated into any component for illuminated medical infusion according to embodiments of the present invention including filters, valves, access ports, or any other component for medical infusion that will occur to those of skill in the art.

In the examples presented above, the light transmission channel is described as being directed to illumination without additional functionality imparted to the light transmission channel. In fact, in additional embodiments of the present invention, the light transmission channel may also provide more functionality. The light transmission channel may, for example, also be used to transmit data. In embodiments where the light transmission channel is implemented as an optical fiber, the light transmission channel may provide data transmission between any number of components, such as data communications from an infusion pump to a manifold, other line impediments, and so on as will occur to those of skill in the art. Furthermore, electroluminescence and pulsing with technologies such as those described above and others may further provide the ability to transmit data through the light transmission channel as will occur to those of skill in the art. Components receiving data transmission typically also include the functionality for replicating the data received and retransmitting that data to one or more other components useful in illuminated medical infusion according to embodiments of the present invention.

Data that may be usefully transmitted across the light transmission channel may include the flow rate of the medical infusion, a representation or identification of the drug or fluid infused, physical parameters of the system configuration of the medical infusion set-up generally, specific gravity of the medical infusion, pressure of the medical infusion, status of the medication, identification of the patient, medical practitioner or other operative, trigger alarms such as changes in pressure or flow rate, schedule of various changes in the set of up the medical infusion or any other data that will occur to those of skill in the art. Furthermore, data transmission is not limited to data communications across the light transmission channel. Wireless communications may also be implemented for data communications among one or more components of illuminated medical infusion according to embodiments of the present invention including infusion pumps, inline impediments, manifolds and many others as will occur to those of skill in the art.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. An illuminating medical infusion system for infusion line identification comprising:
    a medical infusion pump;
    an illuminating infusion line originating from the medical infusion pump;
    wherein the illuminating infusion line has a source of illumination located at the medical infusion pump; and
    wherein the source of illumination is coupled with the medical infusion pump;
    wherein the illuminating infusion line includes an integrated fluid transmission channel and light transmission channel; the light transmission channel being formed continuous to the exterior of the fluid transmission channel; and
    wherein the proximal end of the fluid transmission channel is connected to the medical infusion pump and the distal end of the fluid transmission channel is connected to a medical entry port to the body of a patient; and
    wherein the fluid transmission channel delivers fluids to the body of the patient; and
    wherein the proximal end of the light transmission channel is connected to the source of illumination that is coupled with the medical infusion pump; the distal end of the light transmission channel terminates at the medical entry port to the body of the patient; and
    wherein the illuminating infusion line provides visible illumination exterior to the body of the patient and along the entire length of the illuminating infusion line;
    wherein the fluid transmission channel and light transmission channel are continuous for the entire length of the illuminating infusion line; and
    wherein the fluid transmission channel includes at least one in-line impediment; and
    wherein the fluid transmission channel traverses through the at least one in-line impediment; and
    wherein the light transmission channel traverses the at least one in-line impediment and provides visible illumination across the at least one in-line impediment by passing exterior to the at least one in-line impediment and being contiguous to the exterior of the at least one in-line impediment.

2. The medical infusion system of claim 1 wherein the source of illumination is a light emitting diode that is coupled with the medical infusion pump.

3. The medical infusion system of claim 1 wherein the source of illumination is an organic light emitting diode that is coupled with the medical infusion pump.

4. The medical infusion system of claim 1 wherein the source of illumination is electroluminescence that is coupled with the medical infusion pump.

5. The medical infusion system of claim 1 wherein the source of illumination is coupled to a exterior housing of the medical infusion pump.

6. The medical infusion system of claim 1 wherein the source of illumination is coupled to a interior housing of the medical infusion pump.

7. The medical infusion system of claim 1 wherein the source of illumination is powered by the medical infusion pump.

8. The medical infusion system of claim 1 wherein the at least one in-line impediment comprises a filter.

9. The medical infusion system of claim 1 wherein the at least one in-line impediment comprises an access port.

10. The medical infusion system of claim 1 wherein the at least one in-line impediment comprises a bolus port.

11. The medical infusion system of claim 1 wherein the at least one in-line impediment comprises a manifold.

12. The medical infusion system of claim 1 wherein the medical infusion pump is comprised of multiple infusion pumps, wherein each medical infusion pump is capable of connection to a separate and individual illuminating infusion line.

13. The medical infusion system of claim 1 wherein the medical infusion pump is equipped with an external power casing in which the light transmission channel of the illuminating infusion line is connected.

14. The medical infusion system of claim 1 wherein the light transmission channel traverses the at least one in-line impediment and provides visible illumination across the at least one in-line impediment by adhering externally to the at least one in-line impediment.

* * * * *